US005741291A

United States Patent [19]

Yoo

[11] Patent Number: 5,741,291
[45] Date of Patent: Apr. 21, 1998

[54] ACUPUNCTURE OF THE BLEEDING

[76] Inventor: Tae Woo Yoo, 807, 1-Dong, Hanyang, Apt. 32-5, Banpo-dong, Seocho-ku, Rep. of Korea

[21] Appl. No.: 650,863

[22] Filed: May 20, 1996

[30] Foreign Application Priority Data

Feb. 23, 1996 [KR] Rep. of Korea ........................ 96-2699

[51] Int. Cl.[6] .................................................... A61B 17/34

[52] U.S. Cl. ........................... 606/189; 606/181; 606/204

[58] Field of Search ............................ 606/181, 185–188, 606/189, 204, 167; 604/192, 194, 263

[56] References Cited

U.S. PATENT DOCUMENTS

| | | | |
|---|---|---|---|
| 4,580,566 | 4/1986 | Hsu | 128/329 A |
| 5,368,047 | 11/1994 | Suzuki et al. | 128/765 |
| 5,569,287 | 10/1996 | Tezuka et al. | 606/182 |
| 5,624,460 | 4/1997 | Yoo | 606/181 X |

*Primary Examiner*—Michael Buiz
*Assistant Examiner*—Nancy Mulcare
*Attorney, Agent, or Firm*—Richard M. Goldberg

[57] ABSTRACT

An acupuncture needle assembly includes an outer tubular member having an upper portion tube with open upper and lower ends, and with an elongated slot in the lower end, and a lower portion tube with open upper and lower ends and secured to the upper portion tube; a plug with an opening secured to the open upper end of the upper portion tube; an operating bar slidably positioned through the plug and in the outer tubular member, and having an upper part extending out through the upper end of the upper portion tube and having helical threads, a lower part for holding one end of a needle such that an opposite end of the needle can extend through the open lower end of the lower portion tube, and a hole in the lower part; a pin secured in the hole in the operating bar and slidable in the elongated slot in the upper portion tube to prevent rotation of the operating bar in the outer tubular member, while permitting axial movement of the operating bar in the outer tubular member; a cap securable to the lower end of the operating bar for securing one end of the needle to the lower end of the operating bar; an adjustment nut threadedly engaged on the upper part of the operating bar, to limit downward movement of the operating bar through the outer tubular member; and a spring biasing the operating bar upwardly in the outer tubular member.

14 Claims, 3 Drawing Sheets

ACUPUNCTURE OF THE BLEEDING

BACKGROUND OF THE INVENTION

The present invention relates to an acupuncture needle assembly for bleeding in order to remove stagnating harmful blood at a wounded part, a bruise, a sprain or to circulate blood harmoniously to overcome swoon, anemia and hypertension.

Specifically, the present invention relates to an acupuncture needle assembly for bleeding that is simple and convenient to use, and which overcomes the problem of an operator becoming uneasy when operating the same for acupuncture of bleeding.

Conventionally, there has been known acupuncture of bleeding as disclosed by the present applicant in Korean Utility Model No. 90-6233. However, an operator seized with fear, due to stabbing a patient in the affected area to produce bleeding, had trouble making deep wounds or required further re-operations. An acupuncture appliance of the hand for use of herb medicine has also been known in Korean Utility Model No. 89-5270. This operates to find formed veins in the affected part of the palm of the hand. However, in setting up the raised bar by a spring, after pressurization, there is an inner space having a needle with a magnet of a ring shape, and therefore, this device is very different from the present invention.

SUMMARY OF THE INVENTION

The present invention was derived to solve the above problems. In this regard, there is an elastic spring positioned in upper and lower portion tubes. An adjustment nut which is located on the upper part of an operation bar can adjust the length of the operation bar in the upper and lower portion tubes, and thereby, the distance of travel of the needle. The operation bar is operated by finger pressure at the head portion on the upper end of the operation bar, in order to perform a one time acupuncture of bleeding. Thus, the operation can be performed simply and sanitarily.

With the present invention, the operation bar for injecting a needle for removing harmful blood, has an elastic spring therearound, which spring is positioned in the upper and lower portion tubes in surrounding relation to the operation bar. After the adjustment nut, which is located in the upper part of the operation bar is adjusted to change the operating length of the operating bar, pressure is applied to the head portion. Thus, an operator can execute the acupuncture operation exactly and simply without fear.

DESCRIPTION OF THE PREFERRED EMBODIMENT

The acupuncture needle assembly 1 of the present invention is described in detail with respect to the accompanying drawings and example.

Figure 1:
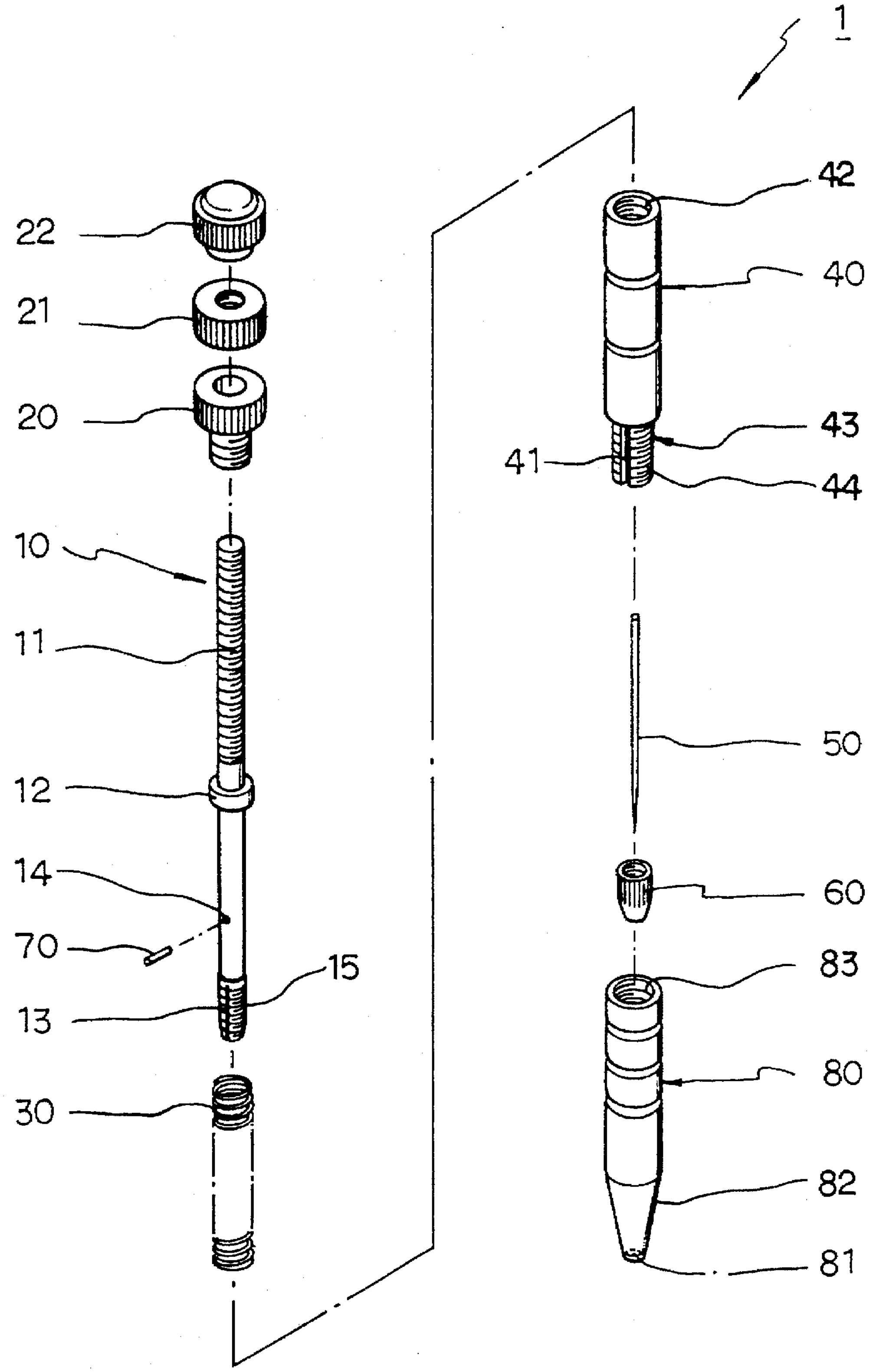
FIG. 1 is an exploded perspective view of the present invention.
Figure 2A:
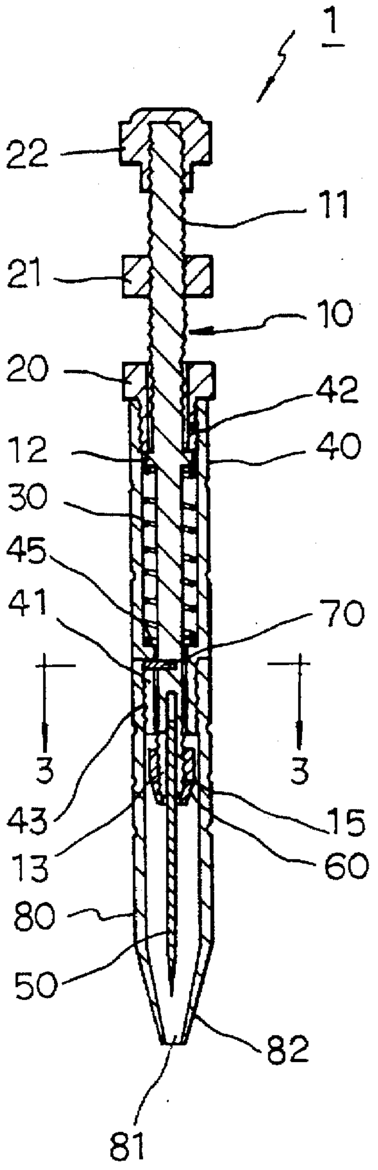
FIG. 2A is a longitudinal sectional view of the present invention prior to the operating state.
Figure 2B:
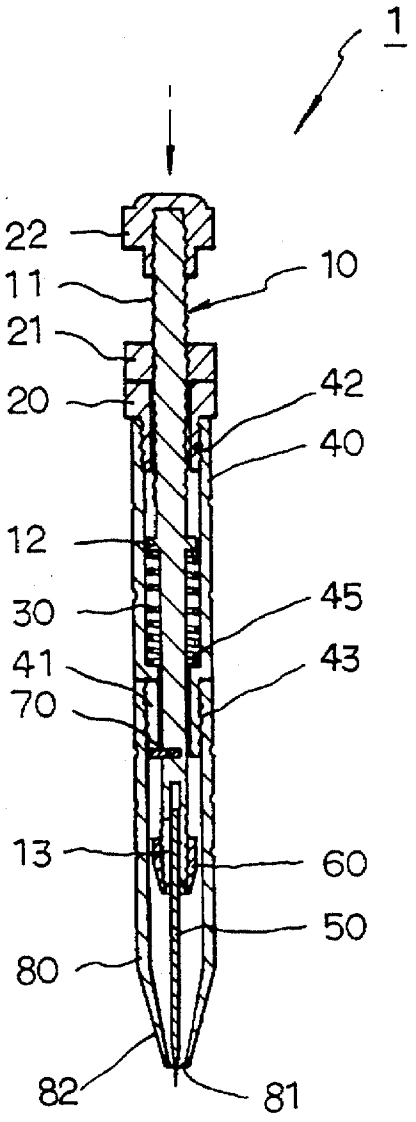
FIG. 2B is a longitudinal sectional view of the present invention showing the operating state.
Figure 3:
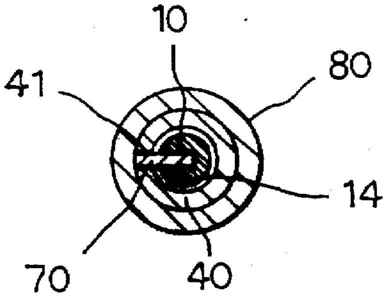
FIG. 3 is an enlarged cross-sectional view of FIG. 2A, taken along line 3—3 thereof.

As shown in FIGS. 2A and 2B, an adjustment nut 21 is threadedly engaged on external helical thread portion 11 for threaded movement therealong, and a head portion or stopper nut 22 is threadedly secured to the upper end of external helical thread portion 11 of operating bar 10.

A keeper or annular shoulder 12 is formed substantially midway along operating bar 10, immediately below external helical thread portion 11. A coil spring 30 is positioned around the opposite lower part of operating bar 10, with the upper end thereof in abutment against keeper 12. A needle 50 is fit in a split slot 13 at the lower end of operating bar 10, with needle 50 fixed in split slot 13 by a cap 60 threadedly tightened on exterior threads 15 at the lower end of operating bar 10. Further, a radially oriented hole 14 is provided in the lower part of operating bar 10 above split slot 13.

An upper portion tube 40 is provided which is open at upper and lower end thereof. A plug 20 having external threads thereon is threadedly secured to internal threads 42 at the upper end of upper portion tube 40. Operating bar 10, thus assembled, is then inserted through the open upper end of upper portion tube 40, and particularly, through the through hole in plug 20.

An elongated slot 41 is located in a lower reduced diameter part 43 of upper portion tube 40, with such lower part having external helical threads 44. A pin 70 penetrates through elongated slot 41 into hole 14 in the lower part of operating bar 10.

It will be appreciated that lower part 43 with external helical threads 44, has a smaller inner diameter than the remainder of upper portion tube 40 so as to form an inner annular shoulder 45. Thus, spring 30 is captured between annular shoulder 12 of operating bar 10 and inner annular shoulder 45 of upper portion tube 40, as shown best in FIGS. 2A and 2B. Spring 30 thereby functions to apply an upward force on operating bar 10. Thus, any pressure applied to head portion or stopper nut 22 to depress operating bar 10, is against the force of spring 30.

With the structure thus assembled, needle 50, which is fixed in split slot 13 by cap 60 so as not to move, can easily be changed by loosening cap 60 and replacing the needle with a new needle 50, which is then fixed again in position by means of cap 60.

A lower portion tube 80 has a tapered lower end 82 with a needle opening 81, and an open upper end with internal helical threads 83. External helical threads 44 of lower part 43 of upper portion tube 40 are threadedly engaged with internal helical threads 83 of lower portion tube 80 to secure upper and lower portion tubes 40 and 80 together in axial alignment.

Prior to use, the action distance or operation depth of needle 50 can be adjusted by threadedly moving adjustment nut 21 up or down along external helical thread portion 11 of operating bar 10, as shown best in FIGS. 2A and 2B, to adjust the distance that the tip of needle 50 extends from needle opening 81 when operating bar 10 is pressed down. However, during such adjustment, pin 70 is limited to axial movement in elongated slot 41, so that it can only move up and down, but cannot rotate right or left. Thus, even if adjustment nut 21 is turned by mistake when changing a needle 50, pin 70 and operating bar 10 can only move up and down. With the present invention, the effective operation depth of needle 50 can thereby easily be set without mistake.

Figure 4:
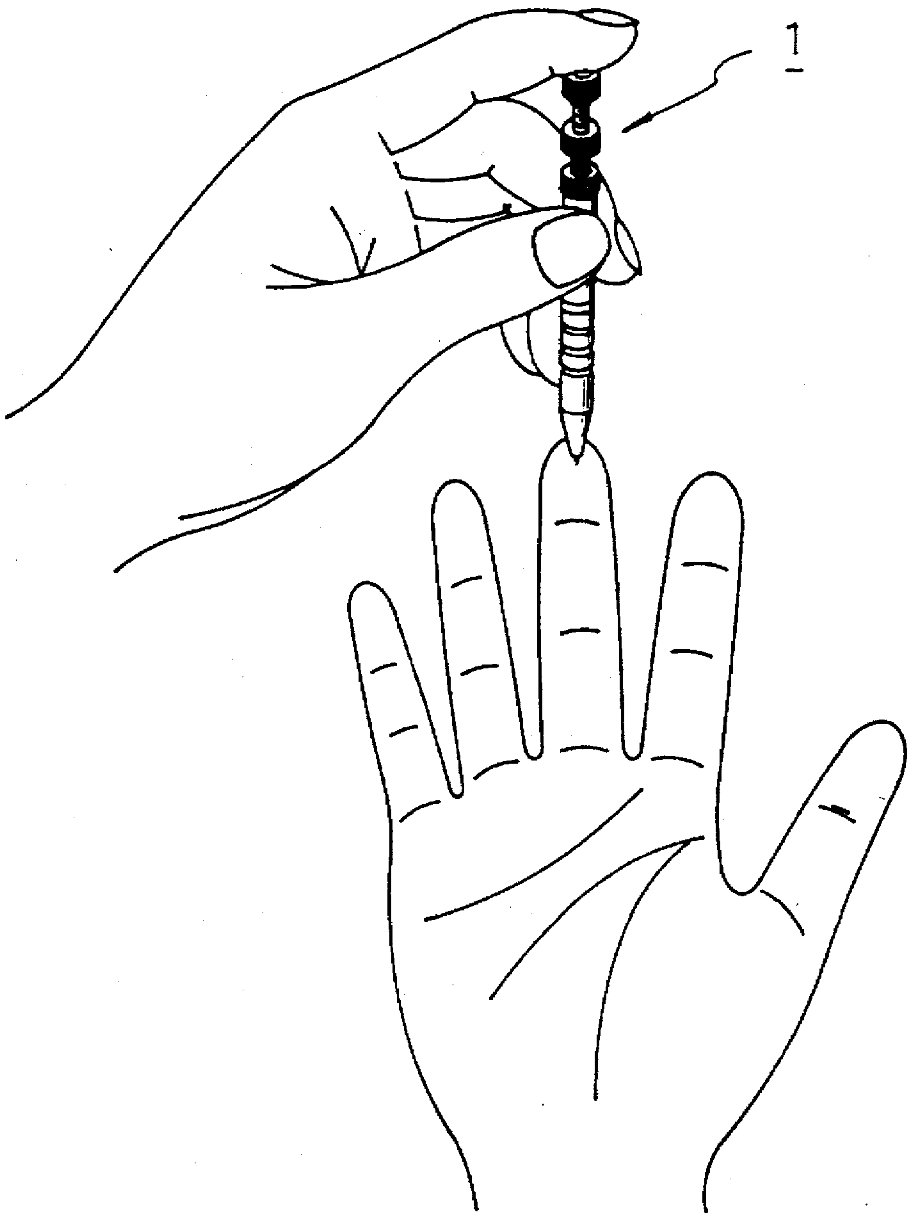
FIG. 4 is a perspective view of the present invention, showing use of the same on a person's finger during the operating state thereof.

As shown in FIG. 4, in use of the present invention for performing bleeding acupuncture of an affected body part, the lower end of lower portion tube 80 is placed on the affected body part and head portion 22 is pressed down by the operator's finger. As a result, operation bar 10 descends within upper portion tube 40 and the tip of needle 50 extends out of needle opening 81, as shown in FIG. 2B. Because the distance that the tip of needle 50 extends from opening 81 is limited, an operator does not have any fear when using acupuncture needle assembly 1.

After the operation is completed, the operator removes his finger from head portion 22, whereby spring 30 biases keeper 12, and thereby operating bar 10, upwardly until keeper 12 abuts against the lower edge of plug 20, as shown in FIG. 2A. In this position, needle 50 is retracted through needle opening 81 and housed entirely in the housing of upper portion tube 40 and lower portion tube 80, by the dynamic stability of spring 30. If the user desires, adjustment nut 21 can be moved down to lock needle 50 in such position, that is, to prevent accidental depression of operating bar 10.

Thus, with the present invention, an operator can conveniently and instantly use acupuncture needle assembly 1 on the affected part which requires bleeding, by a mere depression by his finger, without fear.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

What is claimed is:

1. An acupuncture needle assembly comprising:

a portion tube including:
  an open upper end, and
  an open lower end;

an operating bar slidably positioned in said portion tube wherein said operating bar has an upper part extending out through said open upper end, said operating bar having means at a lower end thereof for holding one end of a needle such that an opposite end of said needle can extend through the open lower end of said portion tube;

an adjustment nut positionable at any of a plurality of different positions along said upper part of said operating bar to limit downward movement of said operating bar through said portion tube; and a spring having one end applying a force against said operating bar and an opposite end applying a force against said portion tube, such that the operating bar is upwardly biased by the spring in said portion tube and such that the opposite end of said needle is retracted by the spring into said portion tube;

wherein depression of an upper end of said operating bar causes said operating bar to move downwardly in said portion tube against the force of said spring, by a distance limited by the adjustment nut, such that the opposite end of the needle exits the open lower end of said portion tube by a predetermined distance.

2. An acupuncture needle assembly according to claim 1, wherein said portion tube includes an upper portion tube having said open upper end and a lower portion tube having said open lower end, with said upper portion tube connected to said lower portion tube such that said upper and lower portion tubes are in axial alignment with each other.

3. An acupuncture needle assembly according to claim 2, further comprising a plug secured to the open upper end of said upper portion tube and having a through opening, and said operating bar is slidably positioned through said through opening of said plug.

4. An acupuncture needle assembly according to claim 3, wherein said upper portion tube has an inner shoulder and said spring is restrained at said one end thereof by said plug and at said opposite end thereof by said inner shoulder.

5. An acupuncture needle assembly according to claim 1, wherein said upper part of said operating bar has helical threads thereon, and said adjustment nut is threadedly engaged on said upper part of said operating bar.

6. An acupuncture needle assembly according to claim 1, wherein:
  said portion tube includes an elongated slot therein, and said operating bar has a lower part with a hole therein, and further comprising:
  a pin secured in said hole in said operating bar and slidably positioned in said elongated slot in said portion tube to prevent rotation of said operating bar in said portion tube, while permitting axial movement of said operating bar in said portion tube.

7. An acupuncture needle assembly according to claim 1, further comprising a cap securable to said lower end of said operating bar for securing said one end of the needle to the lower end of said operating bar.

8. An acupuncture needle assembly according to claim 1, further comprising a head portion secured to an upper end of said operating bar.

9. An acupuncture needle assembly according to claim 1, wherein said open lower end of said portion tube is tapered.

10. An acupuncture needle assembly comprising:

an outer tubular member including:
  an upper portion tube extending in an axial direction and having an open upper end and an open lower end, said open lower end having an elongated slot extending in said axial direction, and
  a lower portion tube extending in said axial direction and having an open upper end secured to the open lower end of said upper portion tube, and an open lower end;

a plug secured to the open upper end of said upper portion tube and having a through opening;

an operating bar slidably positioned through said through opening of said plug and in said outer tubular member, said operating bar having:
  an upper part extending out through said open upper end of said upper portion tube and out from said plug, said upper part having helical threads thereon,
  a lower part having a lower end,
  means at the lower end for holding one end of a needle such that an opposite end of said needle can extend through the open lower end of said lower portion tube, and
  a hole in said lower part;

a pin secured in said hole in said lower part of said operating bar and slidably positioned in said elongated slot in said upper portion tube to prevent rotation of said operating bar in said outer tubular member, while permitting axial movement of said operating bar in said outer tubular member;

a cap securable to said lower end of said operating bar for securing said one end of the needle to the lower end of said operating bar;

an adjustment nut threadedly engaged on said upper part of said operating bar so as to be positioned at any of a plurality of different positions along said upper part of said operating bar, to limit downward movement of said operating bar through said outer tubular member;

a head portion secured to an upper end of said operating bar;

a spring having one end applying a force against said operating bar and an opposite end applying a force against said outer tubular member, such that the operating bar is upwardly biased by the spring in said outer tubular member and such that the opposite end of said needle is retracted by the spring into said outer tubular member;

wherein depression of an upper end of said operating bar causes said operating bar to move downwardly in said portion tube against the force of said spring, by a distance limited by the adjustment nut, such that the opposite end of the needle exits the open lower end of said portion tube by a predetermined distance.

11. An acupuncture needle assembly according to claim 10, wherein said plug is threadedly secured to the open upper end of said upper portion tube.

12. An acupuncture needle assembly according to claim 10, wherein said upper portion tube has an inner shoulder and said spring is restrained at said one end thereof by said plug and at said opposite end thereof by said inner shoulder.

13. An acupuncture needle assembly according to claim 10, wherein said open lower end of said lower portion tube is tapered.

14. An acupuncture needle assembly according to claim 10, wherein said cap is removably threaded on said lower end of said operating bar.

* * * * *